United States Patent [19]
Vanhoof et al.

[11] 4,076,833
[45] Feb. 28, 1978

[54] DERIVATIVES OF 1,3-BENZODIOXOLE, THE PREPARATION AND USE THEREOF

[75] Inventors: Pierre M. Vanhoof; Pierre M. Clarebout, both of Brussels, Belgium

[73] Assignee: A. Christiaens Societe Anonyme, Brussels, Belgium

[21] Appl. No.: 756,529

[22] Filed: Jan. 3, 1977

Related U.S. Application Data

[62] Division of Ser. No. 533,558, Dec. 17, 1974, Pat. No. 4,016,284.

[30] Foreign Application Priority Data

Dec. 17, 1973  United Kingdom ............... 58292/73

[51] Int. Cl.² .............................................. A61K 31/36
[52] U.S. Cl. .................................................. 424/282
[58] Field of Search ...................... 260/340.5; 424/282

[56] References Cited

U.S. PATENT DOCUMENTS

| | | | |
|---|---|---|---|
| 3,149,129 | 9/1964 | Gardner et al. | 260/340.5 R |
| 3,969,368 | 7/1976 | Manghisi et al. | 260/340.5 R |
| 3,970,672 | 7/1976 | Manghisi et al. | 260/340.5 R |

*Primary Examiner*—Ethel G. Love
*Attorney, Agent, or Firm*—Sughrue, Rothwell, Mion, Zinn and Macpeak

[57] ABSTRACT

This invention relates to new derivatives of 1,3-benzodioxole, namely 2-[N-($R_1$, $R_2$ aminocarbamoyl)]-phenylaminomethyl-1,3-benzodioxole, in which $R_1$ is hydrogen or a lower alkyl group, $R_2$ is a lower alkyl group and $R_1$ and $R_2$ may also form with the attached nitrogen atom a nitrogenous heterocyclic ring.

The new derivatives of 1,3-benzodioxole are valuable therapeutic agents for the treatment of heart arrhythmy.

3 Claims, No Drawings

DERIVATIVES OF 1,3-BENZODIOXOLE, THE PREPARATION AND USE THEREOF

This is a division of application Ser. No. 533,558, filed Dec. 17, 1974, now U.S. Pat. No. 4,016,284.

SUMMARY OF THE INVENTION

This invention relates to new derivatives of 1,3-benzodioxole, the preparation and use thereof.

The new derivatives of 1,3-benzodioxole according to this invention may be represented by the following general formula:

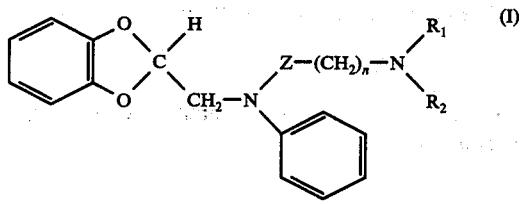

in which Z represents a

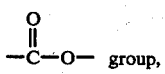

$R_1$ and $R_2$ which may be identical or different represent each a lower alkyl group containing 1 to 4 carbon atoms and $R_1$ may also represent hydrogen, $n$ is equal to 2 or 3.

This invention relates also to the acid addition salts of the compounds of formula I.

The preferred compounds of the formula I are those in which $n$ has the above meanings, $R_1$ and $R_2$ represent a methyl or ethyl group or $R_1$ represents hydrogen whereas $R_2$ represents n methyl or ethyl group, as well as the acid addition salts thereof, such as the hydrochlorides, fumarates, oxalates, etc.

This invention relates also to pharmaceutical compositions containing, as active ingredient, at least one compound of the general formula I, together with a pharmaceutically acceptable carrier.

Finally, the invention relates to a process for preparing the new compounds of formula I.

A preferred compound of formula I is:

-2-[N-(γ-diethylaminopropylcarbamate)]-phenylamino-methyl-1,3-benzodioxole

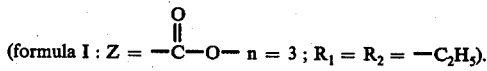

DETAILED DESCRIPTION OF THE INVENTION

It has been surprisingly found that the compounds of the general formula I are very active for the treatment of heart arrhythmia.

Said compounds can be used for the treatment of various heart diseases such as premature heart contractions, ventricular and supraventricular tachycardias either idiopathic or subsequent to a cardiopathia or to a coronary disease, cardiac arrhythmias due to digitalin intoxication, as well as atrial fibrillation and flutter, particularly in the early stage.

It is known (see Koch-Weser, J. Arch. Int. Med. 129; 763, 1972) that none of the presently available antiarrhythmic agents are satisfactory for the prophylaxis of tachycardias and fibrillation of ventricular origin.

The oral activity of the known antiarrhythmic agents, such as procainamide or lidocaine, is either too short leading to multiple day and night administration (for example with procainamide) or too low to be of some practical utility (for example with lidocaine) or their therapeutic activity is conjugated with frequent and dangerous side effects, such as hypotension (with procainamide), sudden death, agranulocytosis or idiosyncrasy.

The compounds of general formula I according to this invention are very active when orally administered, although they may also be administered parenterally. They have also a long activity duration and are not depressant for the myocardial function.

Applicants do not know any orally active antiarrhythmic agents whith does not act at the same time as a depressant of the myocardial function.

The oral antiarrhythmic activity of the compounds of formula I has been proved by tests on rats using aconitine which is a compound causing premature heart contractions and death of the animals.

The method used for these tests is described hereafter:

Animals

Male or female rats with a body-weight ranging from 380 to 450 g.

Aconitine solution 3.12 g aconitine nitrate/1 ml physiological saline.

Solution of the compound to be tested 0.75% in distilled water.

The relative activity between the tested compound and a reference substance (lidocaine, procainamide) is computed in the following way:

$$A(x) = (\overline{X} - \overline{C}/\overline{R} - \overline{C}) \times 100$$

where:

$A(x)$ = activity of tested compound (in %)
$\overline{X}$ = mean dose of aconitine in the animals treated by tested compound
$\overline{C}$ = mean dose of aconitine injected in the untreated animals (controls)
$\overline{R}$ = mean dose of aconitine injected in the animals treated by the reference substances.

The following table gives the results of the evaluation of the antiarrhythmic activity by oral route of an acid addition salt of a prefered compound of formula I, compared to the activity of two well known antiarrhythmic agents (procainamide and lidocaine).

TABLE I

| Compound of example | Formula I | | | Activity in % compared with | |
|---|---|---|---|---|---|
| | Z | n | $N\langle{}^{R_1}_{R_2}\rangle$ | Lidocaine | Procainamide |
| | COO | 3 | diethylamino | 886 | 1131 |

The compounds of the formula I may be administered orally or parenterally.

Oral preparations may be administered under the form of capsules, tablets, pills and the like. Each capsule, tablet or pill may contain from 10 to 200 mg of a compound of formula I as active ingredient, together with pharmaceutically acceptable excipients or carriers.

Parenteral preparations may consist in a solution for perfusion or for intravenous or intramuscular injection. Such a solution may contain from 0.2 per thousand to 2 per thousand of a compound of formula I.

The parenteral preparation may be either a solution which may be directly used for the perfusion and contains a proportion of the active ingredient within the above limits, or a concentrated solution containing 1 to 10% of the active ingredient, said concentrated solution being diluted when administered to a patient.

The initial dose of active ingredient may be of 200 to 800 mg per day during 2 or 3 days, the maintainance dose being of about 25 mg to 300 mg per day.

If a single dose is sufficient for obtaining the therapeutic effect, this dose is generally comprised between 50 and 300 mg.

The active ingredient may be administered at the same time by the parenteral route (for example by perfusion) and by oral route.

This invention relates also to a process for preparing the new compounds of formula I.

The process according to this invention comprises the conversion of a compound of the formula:

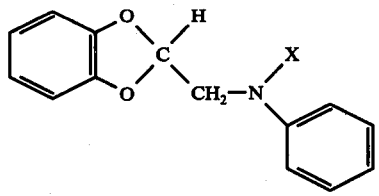

(II), in which X represents a COCl group into a compound of the formula I by aminoalkoxylation in one or two steps.

According to one embodiment of the process of this invention, the compounds of the formula I, in which Z represents a

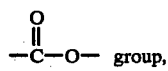

$n = 2$ or 3 and $R_1$ and $R_2$ have the above meanings, may be obtained from a compound of the formula II, in which X represents a

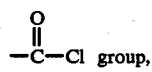

in one step, by reacting said compound with a compound of the formula

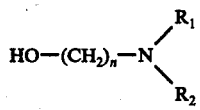

III in which $n$, $R_1$ and $R_2$ have the above meanings.

According to another embodiment of the process according to this invention, the compounds of the formula I, in which Z represents a

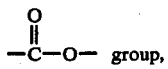

whereas $n$, $R_1$ and $R_2$ have the above meanings, may also be obtained from a compound of the formula II, in which X represents a

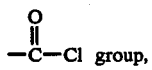

by two steps, the first step comprising the reaction of said compound with a compound of the formula $$HO - (CH_2)_{n'} - Cl \qquad (IV),$$

in which $n' = 2$ or 3, so as to obtain a compound of the formula

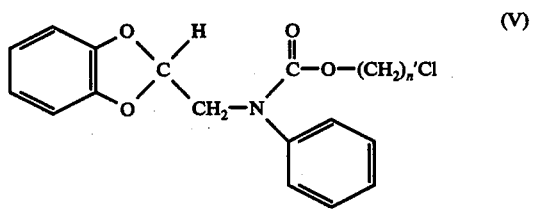

(V)

in which $n'$ has the above meanings, and the second step comprising the reaction of the compound of the formula V with an amine of the formula

(VI)

in which $R_1$ and $R_2$ have the above meanings.

The carbamoyl chloride of 2-phenylamino-methyl-1,3-benzodioxol, which is the compound of formula II, in which X represents a —COCl group, is a new compound which may be prepared by reaction of 2-phenylamino-methyl-1,3-benzodioxole of the formula

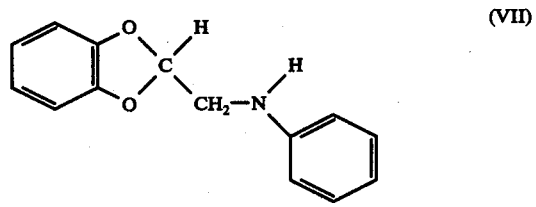

(VII)

with phosgene.

The 2-phenylamino-methyl-1,3-benzodioxole is also a new compound which may be prepared from an ester of 1,3-benzodioxole-2-carboxylic acid, particularly from ethyl 1,3-benzodioxole-carboxylate which is a known compound of the formula:

(VIII)

described by Howard, Hartzfeld, Johnson and Gilman, J.O.C. 22, 1717 (1957), by the following process:

1. Reduction of ethyl 1,3-benzodioxole-2-carboxylate into 2-hydroxymethyl-1,3-benzodioxole of the following formula:

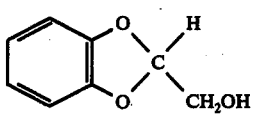
(IX)

this reaction being effected, for example, by means of lithium aluminium hydride (ALLiH$_4$) in ether. The obtained product boils at 90-92° C under a pressure of 0.5 mm.

2. Conversion of the 2-hydroxymethyl-1,3-benzodioxole of formula IX into the mesylate thereof of the following formula:

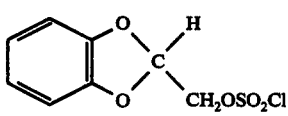
(X)

by reaction with mesyl chloride (CH$_3$SO$_2$Cl)

3. Conversion of the mesylate of formula X into 2-phenylamino-methyl-1,3-benzodioxole of the following formula

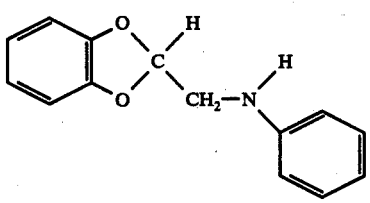
(VII)

by reaction with aniline.

EXAMPLE

The following example illustrates the preparation of the new compounds of formula I.

Preparation of the oxalate of γ-diethylaminopropyl-carbamate of 2-phenylaminomethyl-1,3-benzodioxole.

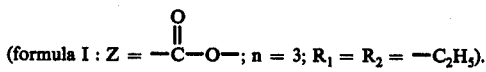

(formula I : Z = —C—O—; n = 3; R$_1$ = R$_2$ = —C$_2$H$_5$).

1. Preparation of the mesylate of 2-hydroxymethyl-1,3-benzodioxole (formula X)

To a solution of 17.8 g of 2-hydroxymethyl-1,3-benzodioxole in 60 ml of pyridine, 10 ml of mesyl chloride are added drop by drop at a temperature comprised between 0° C and —5° C. The obtained mixture is stirred during 1 hour at romm temperature and then poured onto water and ice. After filtration, the filtrate is extracted with ether and dried. The desired product crystallizes when the dried ether solution is concentrated and petroleum ether (B.P. 40°-60° C) is added thereto. The obtained mesylate (22.2 g - yield: 83%) melts at 64°-66° C.

Analysis: % calculated: C, 46.96; H, 4.38; S, 13.9. % found: C, 46.7; H, 4.29; S, 13.7.

2. Preparation of 2-phenylaminomethyl-1,3-benzodioxole (formula VII)

14 g of the mesylate of formula V and 60 ml of aniline are heated and stirred during 4 hours at 135° C. After cooling, 200 ml of ether are added and the formed aniline mesylate is removed. The ether and the free aniline are then removed and the residue is treated with 200 ml of ether. After filtration, a gaseous stream of hydrochloric acid is bubbled into the filtrate. The product is recrystallized from petroleum ether. M.P. 70°-72° C.

Yield: 88%.

Analysis: % calculated: C, 73.99; H, 5.76; N, 6.16. % found: C, 73.6; H, 5.67; N, 6.00.

3. Preparation of the carbamyl chloride of 2-phenyl-aminomethyl-1,3-benzodioxole (formula II : X = —COCl)

4 g of 2-phenylaminomethyl-1,3-benzodioxole, 80 ml of benzene and 100 ml of a toluene solution of phosgene are refluxed during 5 hours. After removal of the solvents, the residue is recrystallized from petroleum ether. M.P. 86°-87° C.

Analysis: % calculated: C, 62.18; H, 4.17; N, 4.83; Cl, 12.23. % found: C, 62.21; H, 4.19; N, 4.99; Cl, 12.30.

4. Preparation of γ-chloropropylcarbamate of 2-phenyl-aminomethyl-1,3-benzodioxole (formula V n' = 3)

4.25 g of the carbamyl chloride of 2-phenylaminomethyl-1,3-benzodioxole and 7 ml of 1-hydroxy-3-chloropropane are stirred and heated during 6 hours at 110° C. After filtration, the solution is concentrated to dryness. The obtained product is directly used in the following step.

5. Preparation of γ-diethylaminopropylcarbamate of 2-phenylaminomethyl-1,3-benzosioxole 4.1 g of γ-chloropropylcarbamate of 2-phenylaminomethyl-1,3-benzodioxole, 17 ml of diethylamine, 17 ml of anhydrous ethanol and 0.4 g of sodium iodide are stirred and heated in an autoclave at 95° C during 24 hours. After cooling and filtration, the solution is concentrated so as to remove the volatile materials and the residue is treated with 50 ml of 2N hydrochloric acid. The obtained solution is made alkaline and extracted with chloroform. After drying of the organic phase and evaporation, the residue is converted into oxalate, which is recrystallized from acetone.

Analysis: % calculated: C, 60.75; H, 6.17; N, 5.9. % found: C, 61; H, 6.44; N, 6.1.

What we claim is:

1. Derivatives of 1,3-benzodioxole of the following general formula

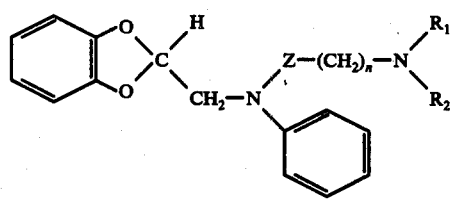

in which Z represents

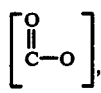

$R_1$ and $R_2$ which may be identical or different represent each a lower alkyl group containing 1 to 4 carbon atoms and $R_1$ may also represent hydrogen, $n$ is equal to 2 or 3, and the pharmaceutically acceptable acid addition salts thereof.

2. Derivative of 1,2-benzodioxole according to claim 1, wherein $R_1$ and $R_2$ represent $C_2H_5$, $n$ represents 3 and Z represents

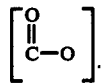

3. A pharmaceutical composition for the treatment of heart arrhythmia which comprises as the active ingredient an amount effective to treat arrhythmia of a derivative according to claim 1 together with a pharmaceutical excipient.

* * * * *